United States Patent
Titlbach et al.

(10) Patent No.: US 12,415,780 B2
(45) Date of Patent: Sep. 16, 2025

(54) HETEROGENEOUS CATALYSTS FOR THE DIRECT CARBONYLATION OF NITRO AROMATIC COMPOUNDS TO ISOCYANATES

(71) Applicant: BASF SE, Ludwigshafen am Rhein (DE)

(72) Inventors: Sven Titlbach, Heidelberg (DE); Andreas Kuschel, Heidelberg (DE); Carlos Lizandara, Ludwigshafen am Rhein (DE); Stephan A. Schunk, Heidelberg (DE); Joerg Rother, Heidelberg (DE); Juergen Bechtel, Heidelberg (DE); Nedko Stefanov Drebov, Ludwigshafen am Rhein (DE); Stefan Maixner, Ludwigshafen am Rhein (DE); Matthias Hinrichs, Ludwigshafen am Rhein (DE); Mohamed Halabi, Ludwigshafen am Rhein (DE); Imke Britta Mueller, Ludwigshafen am Rhein (DE); Michaela Fenyn, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 386 days.

(21) Appl. No.: 17/979,955

(22) Filed: Nov. 3, 2022

(65) Prior Publication Data
US 2023/0131205 A1    Apr. 27, 2023

Related U.S. Application Data

(62) Division of application No. 16/499,686, filed as application No. PCT/EP2018/058616 on Apr. 4, 2018, now Pat. No. 11,512,046.

(30) Foreign Application Priority Data

Apr. 5, 2017 (EP) .................................. 17165019

(51) Int. Cl.
| | | |
|---|---|---|
| C07C 263/14 | (2006.01) |
| B01J 23/62 | (2006.01) |
| B01J 23/644 | (2006.01) |
| B01J 23/656 | (2006.01) |
| B01J 23/889 | (2006.01) |
| B01J 37/02 | (2006.01) |
| B01J 37/03 | (2006.01) |
| B01J 37/08 | (2006.01) |
| B01J 37/16 | (2006.01) |

(52) U.S. Cl.
CPC ............ *C07C 263/14* (2013.01); *B01J 23/62* (2013.01); *B01J 23/626* (2013.01); *B01J 23/628* (2013.01); *B01J 23/6445* (2013.01); *B01J 23/6562* (2013.01); *B01J 23/8892* (2013.01); *B01J 37/0215* (2013.01); *B01J 37/035* (2013.01); *B01J 37/08* (2013.01); *B01J 37/16* (2013.01)

(58) Field of Classification Search
CPC ........ B01J 23/62; B01J 23/626; B01J 23/628; B01J 23/6445; B01J 23/6562; B01J 23/8892; B01J 37/0215; B01J 37/035; B01J 37/08; B01J 37/16; C07C 263/14
USPC ........ 502/353, 327, 329, 330, 332; 420/441, 420/461–463, 466, 501, 557, 563, 576
See application file for complete search history.

(56) References Cited

U.S. PATENT DOCUMENTS

| | | |
|---|---|---|
| 3,523,964 A | 8/1970 | Kober et al. |
| 3,523,966 A | 8/1970 | Ottmann et al. |
| 3,663,278 A | 5/1972 | Blose et al. |
| 3,719,699 A | 3/1973 | McClure et al. |
| 3,737,445 A | 6/1973 | Dodman et al. |
| 3,823,174 A | 7/1974 | Hammond et al. |
| 3,828,089 A | 8/1974 | Hammond et al. |
| 3,979,427 A | 9/1976 | Ottmann et al. |
| 4,207,212 A | 6/1980 | Balabanov et al. |
| 4,332,739 A | 6/1982 | Kervennal et al. |

(Continued)

FOREIGN PATENT DOCUMENTS

| | | |
|---|---|---|
| CN | 1703792 A | 11/2005 |
| DE | 1810828 A1 | 7/1969 |
| DE | 2165355 A | 3/1973 |
| DE | 19635723 A1 | 3/1998 |
| EP | 3606906 B1 | 12/2023 |
| FR | 2120110 A1 | 8/1972 |

(Continued)

OTHER PUBLICATIONS

Behera ("Alloys Based on Intermetallic Compounds" Advanced Materials, p. 617-635, downloaded from https://link.springer.com/chapter/10.1007/978-3-030-80359-9_18#DOI on Jul. 12, 2022; originally published on Nov. 22, 2021) (Year: 2021).

(Continued)

*Primary Examiner* — Patricia L. Hailey
(74) *Attorney, Agent, or Firm* — Faegre Drinker Biddle & Reath LLP

(57) ABSTRACT

A process for preparing an aromatic isocyanate by direct carbonylation of a nitro aromatic compound by reacting the nitro aromatic compound with carbon monoxide in the presence of a catalyst, characterized in that the catalyst contains a multi metallic material comprising one or more binary intermetallic phases of the general formula $A_xB_y$, wherein:
A is one or more element selected from Ni, Ru, Rh, Pd, Ir, Pt and Ag,
B is one or more element selected from Sn, Sb, Pb, Zn, Ga, In, Ge and As,
x is in the range 0.1-10,
y in is in the range 0.1-10.

10 Claims, 3 Drawing Sheets

(56) References Cited

U.S. PATENT DOCUMENTS

| | | | |
|---|---|---|---|
| 4,683,329 A | 7/1987 | Rao | |
| 8,519,207 B2 * | 8/2013 | Armbruester | C07C 5/09 585/277 |
| 10,486,141 B2 * | 11/2019 | Vardon | B01J 35/617 |
| 11,512,046 B2 | 11/2022 | Titlbach et al. | |
| 2012/0225956 A1 * | 9/2012 | Studt | B01J 35/612 977/773 |
| 2013/0184507 A1 | 7/2013 | Giedigkeit et al. | |
| 2015/0004490 A1 * | 1/2015 | Wang | H01M 10/0525 420/560 |
| 2018/0243691 A1 | 8/2018 | Mueller et al. | |

FOREIGN PATENT DOCUMENTS

| | | | | |
|---|---|---|---|---|
| GB | 1315813 A | | 5/1973 | |
| JP | 47-011215 A | | 6/1972 | |
| JP | 2000-192279 A | | 7/2000 | |
| JP | 2000-256764 A | | 9/2000 | |
| JP | 2000-281621 A | | 10/2000 | |
| SU | 368743 A3 | | 1/1973 | |
| SU | 1586510 A3 | | 8/1990 | |
| WO | WO-2004012290 A2 * | | 2/2004 | B01J 23/00 |
| WO | 2017/029165 A1 | | 2/2017 | |
| WO | 2018/185168 A1 | | 10/2018 | |
| WO | WO-2020048852 A1 * | | 3/2020 | C07C 45/38 |

OTHER PUBLICATIONS

Furukawa et al., "Chemoselective Hydrogenation of Nitrostyrene to Aminostyrene over Pd- and Rh-Based Intermetallic Compounds", American chemical society Catalysis, vol. 4, 2014, pp. 1441-1450.

Furukawa et al., "Efficient Catalytic System for Synthesis of trans-Stilbene from Diphenylacetylene Using Rh-Based Intermetallic Compounds", American chemical society Catal., vol. 4, 2014, pp. 3581-3585.

Intermetallics (ChemEurope encyclopedia, downloaded from https://www.chemeurope.com/en/encyclopedia/Intermetallics.html on Jul. 12, 2022) (Year: 2022).

International Preliminary Report on Patentability and Written Opinion of the International Searching Authority issued on Oct. 8, 2019, in PCT/EP2018/058616, 7 pages.

International Preliminary Report on Patentability received for PCT Patent Application No. PCT/EP2018/058616, mailed on Oct. 17, 2019, 8 pages.

International Search Report and Written Opinion issued on Jun, 1, 2018 in PCT/EP2018/058616 filed on Apr. 4, 2018.

International Search Report and Written Opinion received for PCT Patent Application No. PCT/EP2018/058616, mailed on Jun. 1, 2018, 12 pages.

Johnston et al., "Electrical Properties of Some Compounds Having The Pyrite or Marcasite Structure", Journal of The Less-Common Metals, vol. 8, 1965, pp. 272-287.

Patel ("Alloys and Inter-metallic Compounds", p. 1-15, downloaded from http://vpsciencecollege.edu.in/index.php/chemistry-repo/category/11-dr-d-m-patel on Jul. 14, 2022; originally uploaded on Jun. 3, 2019) (Year: 2019).

Furukawa, S., eta al., "Selective Hydrogenation of Functionalized Alkynes to (E)-Alkenes, Using Ordered Alloys as Catalysts," ACS Catalysis, vol. 6, No. 3, pp. 2121-2125 (2016).

Komatsu, T., et al., "Intermetallic Compound Nanoparticles Dispersed on the Surface of Oxide Support as Active and Selective Catalysts," Materials Traansactions, vol. 56, Issue 4, pp. 460-467 (2015).

* cited by examiner

HETEROGENEOUS CATALYSTS FOR THE DIRECT CARBONYLATION OF NITRO AROMATIC COMPOUNDS TO ISOCYANATES

CROSS-REFERENCE TO RELATED APPLICATIONS

This application is a division of U.S. application Ser. No. 16/499,686, filed Sep. 30, 2019, which is a National stage application (under 35 U.S.C. § 371) of International Application No. PCT/EP2018/058616, filed Apr. 4, 2018, which claims benefit of European Application Ser. No. 17/165,019.5, filed Apr. 5, 2017, all of which are incorporated herein by reference in their entirety.

CROSS-REFERENCE TO RELATED APPLICATIONS

This application is a division of U.S. application Ser. No. 16/499,686, filed Sep. 30, 2019, which is a National stage application (under 35 U.S.C. § 371) of International Application No. PCT/EP2018/058616, filed Apr. 4, 2018, which claims benefit of European Application No. 17165019.5, filed Apr. 5, 2017, all of which are incorporated herein by reference in their entirety.

The present invention relates to heterogeneous catalysts for the direct carbonylation of nitro aromatic compounds to aromatic isocyanates and to a process for the direct carbonylation of nitro aromatic compounds to aromatic isocyanates.

The direct carbonylation of nitro aromatic compounds to the corresponding aromatic isocyanates with homogeneous catalysts is reported in the literature. $PdCl_2(pyridine)_2$ and $Fe(Cyclopentadienyl)_2$ as co-catalyst achieved a selectivity to toluylendiisocyanate (TDI) of 9 to 67% at a dinitrotoluene (DNT) conversion of 82% to 100% as described in (DE19635723A1. Major problems that prevent a commercial use are low turnover numbers, difficult catalyst separation, drastic reaction conditions (T=250° C., p=200-300 barg), the formation of by-products and the polymerization of TDI.

Known in the art is a catalyst employed for the carbonylation of 2,4-dinitrotoluene comprising a mixture of a palladium complex with isoquinoline and $Fe_2Mo_7O_{24}$, as disclosed in DE 2165355. 2,4-toluylendiisocyanate is obtained in a maximum yield of 70% at a 100% conversion of the starting compound 2,4-dinitrotoluene. When pyridine is used instead of isoquinoline, the yield is 21-76% at 83-100% conversion of the starting compound, as disclosed in FR 2,120,110. Also known are catalysts for the carbonylation of aromatic nitro compounds containing $Pd(pyridine)_2Cl_2$ and $MoO_3$ or $Cr_2O_3/Al_2O_3$, as disclosed in U.S. Pat. Nos. 3,823,174, and 3,828,089, respectively. A further homogeneous-heterogeneous catalyst for the synthesis of aromatic monoisocyanates, in particular phenyl isocyanate, is $PdCl_2/V_2O_5$, as disclosed in U.S. Pat. No. 3,523,964. In stark contrast to the current invention the systems described in the aforementioned documents are not truly heterogeneous and correspond to a hybrid system comprising homogenous and heterogeneous components. The drawback is that palladium chloride is present in the liquid phase, which necessitates a complicated system for its separation and regeneration.

Only few heterogeneous catalysts for the carbonylation of DNT to TDI are reported in the literature. U.S. Pat. No. 4,207,212 reports $PdO/MoO_3/ZnO$ as a highly active and selective catalyst for DNT carbonylation. All examples of this patent were carried out in the presence of pyridine as additive. This fact leads to the assumption that the formation of pyridine complexes is needed for achieving the carbonylation of the nitroarenes using these catalysts.

Besides direct conversion of nitroaromatics into isocyanates an indirect conversion with nitrosoaromatic as separable intermediate is also known. The conversion of nitroarenes into nitrosoarenes as well as the conversion of nitrosoarenes into aromatic isocyanates in the presence of carbon monoxide is reported in the literature as two separate reactions. This is also the case if the parent nitroarene has more than one nitro-group. Since the current invention enables direct synthesis of isocyanates, but also the indirect synthesis of isocyanates with nitrosoaromatics as stable intermediates. The corresponding literature is cited below.

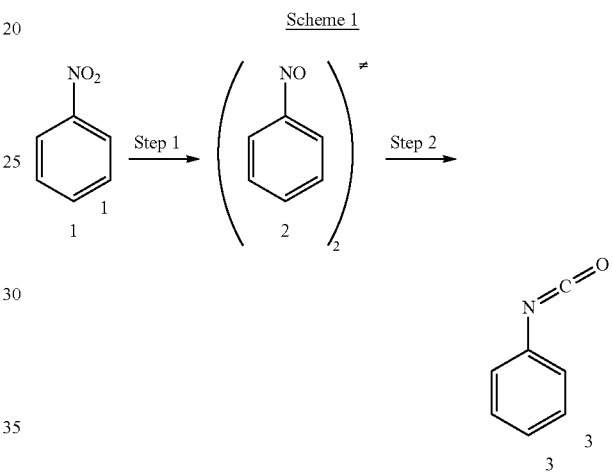

Production of nitrosoarenes corresponding to Step 1 (Scheme 1), which can be also seen as selective reduction of nitrobenzene to nitrosobenzene, is possible with Mn-containing catalysts. DE1810828 discloses catalysts systems of general formula $M_xMn_yO_z$, wherein M is Co, Fe, Pb or Ag, as selective reduction catalyst for nitrobenzene to nitrosobenzene. The oxidic compound comprising Mn and Pb in the ratio of 70/30 provides yields of 4.53% of nitrosobenzene per hour of reaction.

Conversion of nitrosobenzene into isocyanate corresponding to Step 2 (Scheme 1) with the same Mn-containing system is not reported. Carbonylation of nitrosoarenes to aromatic isocyanates corresponding to the reaction 2 (Scheme 1) can be carried out with heterogeneous catalyst comprising one or more of Pd, Rh and Ir supported on $Al_2O_3$, as reported in U.S. Pat. No. 3,979,427.

GB 1 315 813 A describes the heterogeneously catalyzed carbonylation of nitroso- and nitroaromatic compounds to isocyanates in the presence of physical mixtures of $M_xMn_yO_z$, wherein M is Fe, Ag or Pb, with platinum group metals selected form Pd, Ru and Rh supported on carriers such as carbon or pumice. Nitrobenzene is carbonylated to phenyl isocyanate in the presence of a physical mixture of $Pb_xMn_yO_z$, and 5% Rh on carbon. The reported isocyanate yield is 4.5% after 2 h at 190° C.

The object of the present invention is to provide heterogeneous catalysts having high activity and selectivity for the heterogeneously catalyzed process enabling synthesis of isocyanates via direct carbonylation. Direct carbonylation in the sense of the present invention is to be understood as carrying out reaction steps 1 and 2 in a one pot manner without isolation of intermediates. However, the intermediates like nitroso compounds or partially carbonylated nitro aromatic compounds may be obtained as a result of an incomplete reaction.

The goal of the present invention is to provide a process for the carbonylation of nitroaromatic compounds to the corresponding isocyanate showing significant improvement in activity and selectivity.

Composition of Multi Metallic Material

The object of the invention is solved by a catalyst for the direct carboxylation of a nitro aromatic compound to the corresponding aromatic isocyanate and a process for preparing an aromatic isocyanate by direct carboxylation of a nitro aromatic compound in the presence of the catalyst.

The process according to the invention is performed as a heterogeneous catalyzed process In such a heterogeneous catalyzed process the catalyst and reactant(s)/product(s) are in different phases, which are in contact with each other. The reactant(s)/product(s) are in the liquid phase and gas phase, whereas the catalyst will be in a solid phase. The reaction will take place at the interphase between liquid phase, gas phase and solid phase.

The process according to the invention is carried out in the presence of a catalyst. The catalyst
comprises a multi metallic material comprising one or more binary intermetallic phases of the general formula $A_xB_y$ wherein
A is one or more elements selected from Ni, Ru, Rh, Pd, Ir, Pt and Ag,
B is one or more elements selected from Sn, Sb, Pb, Zn, Ga, In, Ge and As,
x in $A_xB_y$ is in the range 0.1-10, preferably from 0.2 to 5, more preferably from 0.5 to 2,
y in $A_xB_y$ is in the range 0.1-10, preferably from 0.2 to 5, more preferably from 0.5 to 2.

More preferred multi metallic materials comprise one or more of binary intermetallic phases of the general formula $A_xB_y$ wherein
A is one or more elements selected from Ni, Rh, Pd, Ir and Pt,
B is one or more elements selected from Sn, Sb, Pb, Ga and In,
x in $A_xB_y$ is in the range 0.1-10, preferably from 0.2 to 5, more preferably from 0.5 to 2,
y in $A_xB_y$ is in the range 0.1-10, preferably from 0.2 to 5, more preferably from 0.5 to 2.

Even more preferred multi metallic materials comprise one or more binary intermetallic phases of the general formula $A_xB_y$ wherein
A is Rh,
B is one of more elements of Pb, Sn or Sb,
x in $A_xB_y$ is in the range 0.1-10, preferably from 0.2 to 5, more preferably from 0.5 to 2,
y in $A_xB_y$ is in the range 0.1-10, preferably from 0.2 to 5, more preferably from 0.5 to 2.

The object of the invention is further solved by providing a continuous, heterogeneous process using a liquid and gas feed together with the multi metallic material.

In general, a multi metallic material can contain or consist of one or more binary intermetallic phases as of the general formula $A_xB_y$ as specified hereinbefore. Furthermore, a multi metallic material is defined as a material comprising at least two different metals in a macroscopically homogeneous phase. In general, multi metallic materials contain at least 85 wt.-%, preferably at least 90 wt.-% and more preferably 95 wt.-% of one or more intermetallic phases of the general formula $A_xB_y$. The multi metallic material can contain one or more other components C wherein component C can consist of or contain A and/or B not being part of the intermetallic compound $A_xB_y$. Component C can also comprise or consist of one or more metallic or non-metallic elements. Preferably component C comprises O, N, C, H, Li, Na, K, Rb, Cs, Mg, Ca, Sr, Ba, Ti, Mn, Fe, Co, Ni, Zn, Ga. In a more preferred embodiment component C comprises O, N, C, H, Mg, Ca, Mn, Fe, Co, Ni, Zn, Ga.

An intermetallic phase or intermetallic compound in terms of this invention is a compound made from at least two different metals in an ordered or partially ordered structure with defined stoichiometry. The structure can be similar or different to the structure of the pure constituent metals. Examples for intermetallic compounds are ordered, partially ordered and eutectic alloys, Laves-phases, Zintl-phases, Heussler-phases, Hume-Rothary-phases, and other intermetallic phases known to the skilled in the art. Also included are compounds comprising elements belonging to the group of semimetals, like selenides, tellurides, arsenides, antimonides, silizides, germanides and borides.

Examples for intermetallic phases according to this invention are RhPb, $RhPb_2$, $Rh_4Pb_5$, $Rh_2Sn$, RhSn, $RhSn_2$, $RhSn_4$, $Rh_2Sb$, RhSb, $RhSb_2$, $RhSb_3$, RhGa, $Rh_{10}Ga_{17}$, $Rh_3Ga_5$, $Rh_2Ga_9$, $Rh_4Ga_{21}$, $Rh_3Ga_{16}$, $RhGa_3$, $RhIn$, $RhIn_3$, $Rh_5Ge_3$, $Rh_2Ge$, RhGe, $Rh_{17}Ge_{22}$, $RhGe_4$, IrPb, IrSn, $Ir_5Sn_7$, $IrSn_2$, $Ir_3Sn_7$, $IrSn_4$, IrSn, $Ir_5Sn_7$, $IrSn_2$, $Ir_3Sn_7$, $IrSn_4$, $Pd_3Pb$, $Pd_{13}Pb_9$, $Pd_5Pb_3$, PdPb, $Pd_3Sn$, $Pd_{20}Sn_{13}$, $Pd_2Sn$, PdSn, $Pd_5Sn_7$, $PdSn_2$, $PdSn_3$, $PdSn_4$, $Pd_3Sb$, $Pd_{20}Sb_7$, $Pd_5Sb_2$, $Pd_8Sb_3$, $Pd_2Sb$, PdSb, $PdSb_2$, $Pd_2Ga$, $Pd_5Ga_2$, $Pd_5Ga_3$, PdGa, $PdGa_5$, $Pd_7Ga_3$, $Ru_2Sn_3$, $RuSn_2$, $Ru_3Sn_7$, RuSb, $RuSb_2$, $RuSb_3$, NiPb, $Ni_3Sn_4$, $Ni_3Sn_2$, $Ni_3Sn$, NiSn, $Ni_5Sb_2$, $Ni_3Sb$, $NiSb_2$ and $NiSb_3$, wherein RhPb, $RhPb_2$, RhSb, $Rh_2Sb$, $RhSb_2$ and $Rh_2Sn$ are the preferred ones.

The presence of intermetallic phases within the multi metallic material can be detected by standard methods for characterizing solids, like for example electron microscopy, solid state NMR or Powder X-Ray Diffraction (PXRD), wherein PXRD-analysis is preferred.

In general, the form in which the invented multi metallic material is provided is not limited.

The multi metallic material can be used as single compound or in ad mixture with other compounds, wherein deposition on a support by methods comprising shallow bed impregnation, spray impregnation, incipient wetness impregnation, melt impregnation and other impregnation methods known to the skilled in the art are preferred. A description how to deposit a multi metallic material on a support is given below.

A support material in terms of this invention can be a crystalline or amorphous oxidic material. This includes binary and polynary oxides alike. Examples for suitable binary oxides are: $Al_2O_3$, CaO, $CeO_2$, $Ce_2O_3$, $Fe_2O_3$, $La_2O_3$, MgO, $MnO_2$, $Mn_2O_3$, $SiO_2$, $TiO_2$, $Ti2O_3$, $ZrO_2$ and ZnO. This specially includes non-stoichiometric or mixed valent oxides wherein the non-oxygen element is present in more than one oxidation state like: $CeO_{2-x}$, $WO_x$, $Fe_{0.95}O$ $Mn_3O_4$, $Fe_3O_4$, $Ti_4O_7$ and other non-stoichiometric oxides known to the expert. Also included are polynary oxides like for example $MgAl_2O_4$, $LaAlO_3$, $CaTiO_3$, $CeZrO_4H_2Al_{14}Ca_{12}O_{34}$. Also included are physical mixtures of binary, polynary and non-stoichiometric oxides.

Also embodied in the group of oxidic supports are zeolite-supports as specified below. This includes supports comprising one or more zeolites, microporous molecular sieves, alumosilicates and alumophosphates as well as mixtures of zeolites with binary, polynary and or nonstoichiometric oxides. Generally, it is conceivable that the zeolitic framework type is one of ABW, ACO, AEI, AEL, AEN, AET, AFG, AFI, AFN, AFO, AFR, AFS, AFT, AFV, AFX, AFY, AHT, ANA, APC, APD, AST, ASV, ATN, ATO, ATS, ATT, ATV, AVL, AWO, AWW, BCT, BEA, BEC, BIK, BOF, BOG, BOZ, BPH, BRE, BSV, CAN, CAS, CDO, CFI, CGF, CGS, CHA, -CHI, -CLO, CON, CSV, CZP, DAC, DDR, DFO, DFT, DOH, DON, EAB, EDI, EEI, EMT, EON, EPI, ERI, ESV, ETR, EUO, *-EWT, EZT, FAR, FAU, FER, FRA, GIS, GIU, GME, GON, GOO, HEU, IFO, IFR, -IFU, IFW, IFY, IHW, IMF, IRN, IRR, -IRY, ISV, ITE, ITG, ITH, *-ITN, ITR, ITT, -ITV, ITW, IWR, IWS, IWV, IWW, JBW, JNT, JOZ, JRY, JSN, JSR, JST, JSW, KFI, LAU, LEV, LIO, -LIT, LOS, LOV, LTA, LTF, LTJ, LTL, LTN, MAR, MAZ, MEI, MEL, MEP, MER, MFI, MFS, MON, MOR, MOZ, *MRE, MSE, MSO, MTF, MTN, MTT, MTW, MVY, MWF, MWW, NAB, NAT, NES, NON, NPO, NPT, NSI, OBW, OFF, OKO, OSI, OSO, OWE, -PAR, PAU, PCR, PHI, PON, POS, PSI, PUN, RHO, -RON, RRO, RSN, RTE, RTH, RUT, RWR, RWY, SAF, SAO, SAS, SAT, SAV, SBE, SBN, SBS, SBT, SEW, SFE, SFF, SFG, SFH, SFN, SFO, SFS, *SFV, SFW, SGT, SIV, SOD, SOF, SOS, SSF, *-SSO, SSY, STF, STI, *STO, STT, STW, -SVR, SVV, SZR, TER, THO, TOL, TON, TSC, TUN, UEI, UFI, UOS, UOV, UOZ, USI, UTL, UWY, VET, VFI, VNI, VSV, WEI, -WEN, YUG, ZON, or a mixed type of two or more thereof. More preferably, the zeolitic material comprises, more preferably is, one or more of zeolitic materials having a framework structure of type MFI, MOR, BEA, and FAU.

Further examples for supports are carbon or carbon-like materials like activated carbon, graphite or graphene. Also included are modified carbon-based materials like intercalation compounds and carbides like W—C, B—C, Si—C. Also included are nitrides, borides, silicides, phosphides, antimonides, arsenids, sulfides, selenides and tellurides.

Also included are alloys, solid solution alloys, partial solution alloys and intermetallic compounds are also included as well as compounds referred to be metal compounds in terms of this invention. Also included in the group of supports are binary and polynary oxidic supports comprising one or more elements from the main groups (excluding noble gases and halides), transition elements and or lanthanides in combination with Oxygen and their respective modifications.

The support material can be provided as powder, dispersion, colloid, granulates, shaped bodies like rings, spheres, extrudates, pellets and other shaped bodies known to the skilled in the art.

Preferred support materials are carbon, binary and polynary oxides and mixtures of binary and polynary oxides.

Synthesis of the Multi Metallic Material

The catalyst of the invention can be prepared by a method comprising the steps in the order (i) to (iv):
(i) Providing a metal precursor preferably in the form of a solution;
(ii) Deposition of the metal precursor on a support material, optionally followed by drying;
(iii) Reductive treatment of the composite material;
(iv) Thermal treatment of the composite material.
(i) This step comprises the preparation of the metal precursor by dissolving or diluting a metal containing component like metal salts, colloidal metals or metal organic compounds in a suitable solvent like water, alcohols, polyols, acids, bases and other solvents known to the skilled in the art. This solution can either be prepared as single metal containing solution of A or B or as a multi metal solution containing any concentration of A and B. In a special embodiment an additional solution is prepared containing the promotor component C. In very special embodiment the promotor component can be part of the single metal solution containing A or B or a part of the multi metal solution containing A and B.
(ii) The metal solution(s) prepared in step (i) are brought onto the support material using standard techniques like shallow bed impregnation, spray impregnation, incipient wetness impregnation, melt impregnation and other impregnation methods known to the skilled in the art. The impregnation can be done in a single step using single or multi metal solutions or mixtures of single and multi-metal solutions. The impregnation can also be done in multiple steps using single or multi metal solutions or mixtures of single and multi-metal solutions in multiple steps. The invention also encloses precipitation techniques wherein the carrier is prepared in situ from the metal solutions or in a separate step. This step also includes one or more drying steps (iia).

The product of step (ii) or respectively step (iia) is a composite material.
(iii) The reductive treatment involves exposing the composite material obtained in step (ii) or respectively step (iia) to a reducing agent or reducing the composite material by thermal reduction. This reducing agent can be provided in solid, liquid or gaseous form. The reducing step can be carried out with or without performing step (iia) before. Reducing agents in terms of this invention are gases like for example $H_2$, CO and gaseous hydrocarbons like $CH_4$, $C_2H_4$ and other reducing gases known to the skilled worker, liquid reducing agents like alcohols, hydrocarbons and amines like for example polyols and hydrazine as well as reducing agents provided in solid form like for example metal powder.
(iv) The thermal treatment of the reduced composite material is done by heating the reduced composite material taken from step (iii) to a desired temperature under chemically inert conditions wherein the gas mixture present does not contain any reactive components that can undergo chemical reaction with the composite material. Particularly the mixture should not comprise oxidizing agents like for example oxygen, water, $NO_x$, halides or there like. The heating can be performed by any method suited to heat solids or wet solids like heating in muffle furnaces, microwaves, rotary kilns, tube furnaces, fluidized bed and other heating devices known to the person skilled in the art.

In a particular embodiment, steps (iii) and (iv) can be combined into a single step by thermal treatment of the composite material in the presence of a reducing agent or at a temperature where thermal reduction occurs.

Process for Synthesis of Isocyanates from Nitroaromatics and Carbon Monoxide

The object of the invention is further solved by a process for preparing an aromatic isocyanate by direct carbonylation of a nitroaromatic compound by reacting the nitroaromatic compound with carbon monoxide in the presence of a catalyst, characterized in that the catalyst contains a multi metallic material as specified hereinbefore comprising one or more of binary intermetallic phases of the general formula $A_xB_y$ with or without a component C.

The Process can be carried out discontinuously or continuously.

The present invention provides new catalytic materials able to catalyze reaction steps 1 and 2 of the overall reaction. The catalytic material is not a physical mixture of two separate catalysts, each of which is able to catalyze only one of the two consecutive reaction steps, as disclosed in GB1315813A, but a catalyst which catalyses both reaction steps 1 and 2.

In the document GB 1 315 813 A heterogeneously catalyzed carbonylation of nitroso- and nitroaromatic compounds to isocyanates is disclosed. However, in contrast to the present invention, physical mixtures of one catalyst of general formula $M_xMn_yO_z$, wherein M is Fe, Ag or Pb, with a second catalyst comprising platinum group metals selected from Pd, Ru and Rh on a support such as carbon or pumice are employed. The reported isocyanate yield is 4.5% after 2 h at 190° C. According to the present invention, the single multi metallic material comprising one or more intermetallic phases $A_xB_y$ provides the required isocyanate with significantly higher selectivity at higher conversions (see Table 4). The presence of one or more intermetallic phases is believed to be responsible for significantly higher yields.

Furthermore, the present invention provides a process for synthesis of isocyanates from nitro aromatics and carbon monoxide comprising the following steps:
a) providing a reagent mixture M1 comprising nitroaromatics and at least one additional component D wherein D comprises a suitable solvent;
b1) Providing a reagent mixture M2 comprising reagent mixture M1 and carbon monoxide or a mixture of carbon monoxide and inert gas G, and/or
b2) providing a reaction mixture R1 comprising the reagent mixture M1 and a carbonylation catalyst comprising the multi metallic material which is described in detail above;
c) contacting the reagent mixture M2 with a carbonylation catalyst comprising preferably consisting of the multi metallic material I) which is described in detail above; and/or
d) contacting the reagent mixture R1 with carbon monoxide or a mixture of carbon monoxide and inert gas G;
e) obtaining a reaction mixture comprising isocyanates.

The above steps may be carried out using either step b1) or b2) or both.

Preferably the concentration of nitroaromatics in the mixture M1 is in the range in the range of from 0.01 wt.-% to 60 wt.-%, more preferred in the range of from 0.1 wt.-% to 50 wt.-%, further preferred in the range of from 1 wt.-% to 40 wt.-%.

Preferably the concentration of component D in mixture M1 is in the range of from 40 wt.-% to 99.99 wt.-%, more preferred in the range of from 50 wt.-% to 99.9 wt.-%, and further preferred in the range of from 60 wt.-% to 99 wt.-%.

Suitable nitroaromatic compounds (or nitroaromatics) to be reacted according to this invention are single or polyaromatic compounds with one or more nitro groups like nitrobenzene, dinitrobenzene, nitrotoluene, dinitrotoluene, trinitrotoluene, nitronaphthaline, nitroanthracene, nitrodiphenyl, bis(nitrophenyl)methane and further single and polyaromatic compounds having one or more nitro groups. The nitroaromatic compounds may also contain other functional groups. In terms of this invention functional groups are substituents connected to the aromatic ring. Functional groups can contain one or more heteroatoms selected from the group consisting of H, B, C, N, P, O, S, F, Cl, Br and I.

Examples for functional groups are hydroxyl groups, halogens, aliphatic side chains, carbonyl groups, isocyanate groups, nitroso groups, carboxyl groups and amino groups.

Also included are nitroorganic compounds containing one or more nitro groups bonded to an aliphatic chain or side chain or ring, such as 1,6-dinitrohexene or nitrocyclohexene, nitrocyclopentene, nitromethane, nitrooctane, and bis-(nitrocyclohexyl)-methane.

A suitable source of nitroaromatics is any source containing at least partially nitroaromatics. The source can be a nitroaromatic freshly provided into the reagent stream M1. Furthermore, nitroaromatics might be an unreacted nitroaromatic that after separation from the product stream is recycled after one or more reprocessing steps. A nitroaromatic can also be a compound which contains at least one nitro and/or at least one nitroso group which is being recycled after its partial conversion with carbon monoxide. A combination of a freshly provided nitroaromatic and a recycled nitroaromatic can be also utilized. Application of nitroaromatic adducts or precursors as for example nitrosoaromatics is also possible.

Suitable source of carbon monoxide is also any source containing at least partially carbon monoxide. The source can be carbon monoxide freshly provided into the reagent stream M1. Furthermore, carbon monoxide might be an unreacted carbon monoxide that after separation from the product stream is recycled after one or more reprocessing steps. A combination of a freshly provided carbon monoxide and recycled carbon monoxide can be also utilized. Application of carbon monoxide adducts or precursors as for example formic acid is also possible.

In addition to nitroaromatics and optionally carbon monoxide the reagent stream M1 may contain one or more components D comprising solvents S, additives X and inert gases G.

Suitable solvents S are aprotic organic solvents like arenes and substituted arenes such as chlorobenzene, dichlorobenzene, benzene, toluene, 1,2-diphenylebenzene, 1,2-dimethylnaphthalin, hexadecylbenzene, Solvesso 150 ND and Solvesso 200 ND.

Other suitable aprotic solvents are (cyclo)alkanes and substituted (cyclo)alkanes such as n-alkanes, cycloalkanes, chloroform, dichloromethane, diphenylmethane, dibenzyl.

Other suitable solvents are open chain and cyclic ethers such as dioctylether or THF.

Preferred solvents with a boiling point in range from 50° C. to 300° C., more preferred from 100° C. to 275° C., and further preferred from 125° to 255° C.

The solvent can also be an Isocyanate corresponding to the respective nitroaromatic compound.

Suitable inert gases G comprise gases such as nitrogen, helium, neon, argon or carbon dioxide from which nitrogen, argon and carbon dioxide are preferred.

The carbonylation is generally carried out at a temperature in the range of from 50 to 250° C., preferably in the range of from 80 to 190° C., and more preferably in the range of from 100 to 170° C.

Total pressure during the reaction is in the range of from 1 to 200 bar, preferably from 10 to 150 bar and more preferably in the range of from 15 to 100 bar.

The partial pressure of carbon monoxide is in the range of from 1 to 150 bar, preferably in the range of from 1 to 120 bar and more preferably in the range of from 1 to 100 bar.

In general contacting of the reaction mixture M1 with the catalyst comprising preferably consisting of the multi metallic material and with carbon monoxide can be carried out in a continuous or discontinuous manner.

Preferably the invention is conducted in batch reactors, cascade of batch reactors, semibatch reactors or continuous reactors. Suitable reactors are stirred tank reactors, loop reactors, loop-venturi-reactors, loop reactors with reversed flow, oscillatory flow reactors, tube reactors, slurry reactors, packed bed reactors, trickle bed reactors, moving bed reactors, rotary bed reactors, other reactor types known to those skilled in the art and combinations of different reactor types.

In one set up the reaction comprises the following reaction steps:
- a) providing a reagent mixture M1 comprising nitroaromatics and at least one additional component D wherein D comprises a suitable solvent;
- b) providing a reaction mixture R1 comprising the reagent mixture M1 and a carbonylation catalyst comprising the multi metallic material which is described in detail above;
- c) contacting the reaction mixture R1 with carbon monoxide or a mixture of carbon monoxide and inert gas G;
- d) obtaining a reaction mixture comprising isocyanates.

In an alternative set up the reaction steps can also be follows:
- a) Providing a reagent mixture M1 comprising nitroaromatics and at least one additional component D wherein D comprises a suitable solvent;
- b) Providing a reagent mixture M2 comprising reagent mixture M1 and carbon monoxide or a mixture of carbon monoxide and inert gas G, to obtain reagent mixture M2.
- c) Contacting the reagent mixture M2 with a carbonylation catalyst comprising preferably consisting the multi metallic material I) which is described in detail above
- d) Obtaining a reaction mixture comprising isocyanates.

In general reaction mixture R1 contains the carbonylation catalyst comprising the multi metallic material. The concentration of the carbonylation catalyst is in the range of from 0.1 to 10 wt.-%, preferably in the range of 0.1 to 7.5 wt.-%, and more preferably in the range of 0.1 to 5 wt.-%.

In general, the reaction mixture R1 is contacted with carbon monoxide from 0.5 to 24 h, preferably from 2 to 20 h, and more preferably from 4 to 12 h.

In general, within reaction mixture M2 the partial pressure of carbon monoxide is in the range of from 1 to 150 bar, preferably in the range of from 1 to 120 bar and more preferably in the range of from 1 to 100 bar.

PREFERRED EMBODIMENTS

The current invention is further illustrated by the following embodiments and combinations of embodiments as indicated below.

In general, the present invention provides a process for preparation of an aromatic isocyanate by direct carbonylation of a nitroaromatic compound catalyzed by a multi metallic material comprising one or more of binary intermetallic phases of the general formula $A_xB_y$ wherein:
- A is one or more elements selected from the group consisting of Ni, Ru, Rh, Pd, Ir, Pt and Ag;
- B is one or more elements selected from the group consisting of Sn, Sb, Pb, Zn, Ga, In, Ge and As;
- x in $A_xB_y$ is in the range 0.1-10, preferably from 0.2 to 5, and more preferably from 0.5 to 2;
- y in $A_xB_y$ is in the range 0.1-10, preferably from 0.2 to 5, and more preferably from 0.5 to 2.

Preferred catalyst comprises one or more of binary intermetallic phases of the general formula $A_xB_y$ wherein
- A is one or more elements selected from the group consisting of Ni, Rh, Pd, Ir and Pt;
- B is one or more elements selected from the group consisting of Sn, Sb, Pb, Ga and In.

More preferred catalysts comprise one or more binary intermetallic phases of the general formula $A_xB_y$ wherein
- A is Rh;
- B is one of more elements selected from the group consisting of Pb, Sn and Sb.

Preferably, the multi metallic material consist to at least 85 wt.-%, more preferably to at least 90 wt.-% and even more preferably to at least 95 wt.-% of one or more of intermetallic phases $A_xB_y$.

In one embodiment, the multi metallic material contains one or more components C, wherein component C consist or contains A and/or B not being part of the intermetallic compound $A_xB_y$.

In a further embodiment, the multi metallic material contains one or more components C, wherein component C comprise or consists of one or more elements selected from the group consisting of O, N, C, H, Li, Na, K, Rb, Cs, Mg, Ca, Sr and Ba, Ti, Mn, Fe, Co, Ni, Zn, Ga preferably one or more elements from the group consisting of O, N, C, H, Mg, Ca, Mn, Fe, Co, Ni, Zn and Ga.

Preferably, the multi metallic material is deposited on a support material, in general a crystalline or amorphous support material. In a first preferred embodiment, the support material comprises carbon, graphite, graphene or an intercalation compound. In a second preferred embodiment, the support material comprises a carbide, nitride, boride, silicide, phosphide, antimonide, arsenide, sulfide, selenide or telluride. In a third preferred embodiment, the support material comprises one or more of binary and polynary oxides like MgO, CaO, ZnO, $CeO_2$, $SiO_2$, $Al_2O_3$, $TiO_2$, $ZrO_2$, $Mn_2O_3$, $Fe_2O_3$, $Fe_3O_4$, $MgAl_2O_4$, $LaAlO_3$, $CaTiO_3$, $CeZrO_4H_2Al_{14}Ca_{12}O_{34}$ and other binary and polynary oxides known to the skilled in the art in their respective modifications. In a fourth preferred embodiment, the support material comprises, preferably consist of one or more zeolitic materials, wherein the zeolitic material preferably has a framework structure of the type ZSM, MFI, MOR, BEA or FAU.

The support material can be provided in a form comprising powders, dispersions, colloids, granulates, shaped bodies like rings, spheres, extrudates or pellets.

The multimetallic material preferably comprises one or more intermetallic crystalline phases selected from RhPb, $RhPb_2$, $Rh_4Pb_5$, $Rh_2Sn$, RhSn, $RhSn_2$, $RhSn_4$, $Rh_2Sb$, RhSb, $RhSb_2$, $RhSb_3$, RhGa, $Rh_{10}Ga_{17}$, $Rh_3Ga_5$, $Rh_2Ga_9$, $Rh_4Ga_{21}$, $Rh_3Ga_{16}$, $RhGa_3$, RhIn, $RhIn_3$, $Rh_5Ge_3$, $Rh_2Ge$, RhGe, $Rh_{17}Ge_{22}$, $RhGe_4$, IrPb, IrSn, $Ir_5Sn_7$, $IrSn_2$, $Ir_3Sn_7$, $IrSn_4$, IrSn, $Ir_5Sn_7$, $IrSn_2$, $Ir_3Sn_7$, $IrSn_4$, $Pd_3Pb$, $Pd_{13}Pb_9$, $Pd_5Pb_3$, PdPb, $Pd_3Sn$, $Pd_{20}Sn_{13}$, $Pd_2Sn$, PdSn, $Pd_5Sn_7$, $PdSn_2$, $PdSn_3$, $PdSn_4$, $Pd_3Sb$, $Pd_{20}Sb_7$, $Pd_5Sb_2$, $Pd_8Sb_3$, $Pd_2Sb$, PdSb, $PdSb_2$, $Pd_2Ga$, $Pd_5Ga_2$, $Pd_5Ga_3$, PdGa, $PdGa_5$, $Pd_7Ga_3$, $Ru_2Sn_3$, $RuSn_2$, $Ru_3Sn_7$, RuSb, $RuSb_2$, $RuSb_3$, NiPb, $Ni_3Sn_4$, $Ni_3Sn_2$, $Ni_3Sn$, NiSn, $Ni_5Sb_2$, $Ni_3Sb$, $NiSb_2$ and $NiSb_3$. Particularly multi metallic materials contain one or more intermetallic crystalline phases selected from RhPb, $RhPb_2$, RhSb, $Rh_2Sb$, $RhSb_2$ and $Rh_2Sn$.

The multimetallic material of any of the previous embodiments is obtainable by a method comprising the steps (i) to (iv):
- (i) Providing a metal precursor preferably in the form of a solution;
- (ii) Deposition of the metal precursor on a support material;
- (iia) optional drying step;
- (iii) Reductive treatment of the composite material;

(iv) Thermal treatment of the composite material.

In step (i), a mixture comprising a solvent and one or more sources for A, B and C is prepared wherein the solvent comprises one or more of water, alcohols, polyols, acids and bases.

In step (ii), the mixture prepared according to step (i) is brought into contact with the support material using a method selected from shallow bed impregnation, spray impregnation, incipient wetness impregnation and melt impregnation. For solvent removal, a method selected from evaporation, heating or freeze drying is preferably used. Also included are precipitation techniques wherein the carrier material is prepared in situ from the metal solutions or in a separate step. This technique also includes an optional drying step.

The reductive treatment step and thermal treatment steps (iii) and (iv) preferably comprise
- (iii) Contacting the material obtained in step (ii) with one or more of reducing agent or wherein the reducing agent can be provided in solid, liquid or gaseous form and comprise alcohols, hydrocarbons, amines, polyols, Zn-powder, $H_2$, CO, $CH_4$ and $C_2H_4$;
- (iv) Reducing the material obtained in step (iii) by thermal reduction under chemically inert conditions.

The thermal treatment comprises heating the material prepared under chemically inert conditions, preferably under inert gases like gases like nitrogen, argon and helium. The heating can be carried out in muffle furnaces, microwaves, rotary kilns, tube furnaces and fluidized beds.

The multi metallic material and the catalyst containing the multi metallic material according to any of the previous embodiments are used for the direct carbonylation of nitroaromatics to isocyanates.

In general, the process for the synthesis of isocyanates from nitroaromatics and carbon monoxide comprises steps a) to d):
- a) providing a reagent mixture M1 comprising nitroaromatics and at least one additional component D wherein D comprises a suitable solvent;
- b1) Providing a reagent mixture M2 comprising reagent mixture M1 and carbon monoxide or a mixture of carbon monoxide and inert gas G, and/or
- b2) providing a reaction mixture R1 comprising the reagent mixture M1 and a carbonylation catalyst comprising the multi metallic material which is described in detail above;
- c) contacting the reagent mixture M2 with a carbonylation catalyst comprising preferably consisting of the multi metallic material I) which is described in detail above; and/or
- d) contacting the reagent mixture R1 with carbon monoxide or a mixture of carbon monoxide and inert gas G;
- e) obtaining a reaction mixture comprising isocyanates.

The concentration of nitroaromatics in the mixture M1 is in general in the range of from 0.01 wt.-% to 60 wt.-%, more preferred in the range of from 0.1 wt.-% to 50 wt.-%, and further preferred in the range of from 0.1 wt.-% to 40 wt.-%. The concentration of component D in mixture M1 is in general in the range of from 40 wt.-% to 99 wt.-%, more preferred in the range of from 50 wt.-% to 99 wt.-%, and further preferred in the range of from 60 wt.-% to 99 wt.-%.

Suitable nitro aromatic compounds comprise single or polyaromatic compounds with one or more nitro groups: nitrobenzene, dinitrobenzene, nitrotoluene, dinitrotoluene trinitrotoluene, nitronaphthaline, nitroanthracene, nitrodiphenyl, bis(nitrophenyl)methane and further single and polyaromatic compounds having one or more nitro groups. The nitro aromatic compounds may also contain other functional groups. In terms of this invention functional groups are substituents connected to the aromatic ring. Functional groups can contain one or more heteroatoms selected from the group consisting of H, B, C, N, P, O, S, F, Cl, Br and I. Examples for functional groups are hydroxyl groups, halogens, aliphatic side chains, carbonyl groups, isocyanate groups, nitroso groups, carboxyl groups and amino groups.

Also included are nitro organic compounds containing one or more nitro groups bonded to an aliphatic chain, side chain or ring, such as 1,6-dinitrohexene or nitrocyclohexene, nitrocyclopentene, nitromethane, nitrooctane, Bis-(nitrocyclohexyl)-methane.

In preferred embodiments, the nitroaromatic is provided in one or more of aprotic organic solvents selected from chlorobenzene, dichlorobenzene, benzene, toluene, THF, dioctylether, chloroform, dichloromethane, n-alkanes, cycloalkanes, 1,2-diphenylebenzene, 1-phenylnaphthalin, dibenzyl, 1,2-dimethylnaphthalin, diphenylmethane, hexadecylbenzene, tetradecylbenzene dodecylbenzene or Solvesso 150 ND and Solvesso 200 ND.

In general, the boiling point of the one or more aprotic organic solvents is in the range from 50° C. to 300° C., preferably from 100° C. to 275° C., more preferably from 125° to 255° C.

In a particular embodiment the solvent can be the Isocyanate corresponding to the respective nitroaromatic compound.

In general, the production of isocyanates is carried out at a temperature in the range from 50 to 250° C., preferably from 80 to 190° C., more preferably from 100 to 170° C. In general, the production of isocyanates is carried out at a total pressure in the range from 1 to 200 bar, preferably from 10 to 150 bar and more preferably from 15 to 100 bar. The carbon monoxide partial pressure is in general from 1 to 150 bar, preferably from 1 to 120 bar and more preferably from 1 to 100 bar.

In a first embodiment, the isocyanates are produced discontinuously in a batch comprising the steps:
- a) providing a reagents mixture M1 comprising nitroaromatic compounds and at least one additional component D wherein D comprise a suitable solvent;
- b) providing a reaction mixture R1 comprising the reagents mixture M1 and a carbonylation catalyst comprising the multi metallic material which is described above;
- c) contacting the reaction mixture R1 with carbon monoxide or a mixture of carbon monoxide and inert gas G;
- d) obtaining a reaction mixture comprising isocyanates.

In general, the concentration of the carbonylation catalyst the reaction mixture R1 is in the range of from 0.1 to 10 wt.-%, preferably in the range of 0.1 to 7.5 wt.-%, more preferably in the range of 0.2 to 5 wt.-%. The reaction times are in general in the range from 0.5 to 24 h, preferably from 2 to 20 h and more preferably from 4 to 12 h.

In a second embodiment, the isocyanates are produced continuously in a process comprising the steps:
- a) providing a reagent mixture M1 comprising nitroaromatics and at least one additional component D wherein D comprises a suitable solvent;
- b) providing a reagent mixture M2 comprising reagent mixture M1 and carbon monoxide or a mixture of carbon monoxide or a mixture of carbon monoxide and inert gas G, to obtain reagent mixture M2.
- c) contacting the reagent mixture M2 with a carbonylation catalyst comprising preferably consisting the multi metallic material I) which is described in details above d) obtaining a reaction mixture comprising isocyanates.

In general, within reaction mixture M2 the partial pressure of carbon monoxide is in the range of from 1 to 150 bar, preferably in the range of from 1 to 120 bar and more preferably in the range of from 1 to 100 bar.

CROSS-REFERENCE TO RELATED APPLICATIONS

Figure 1:
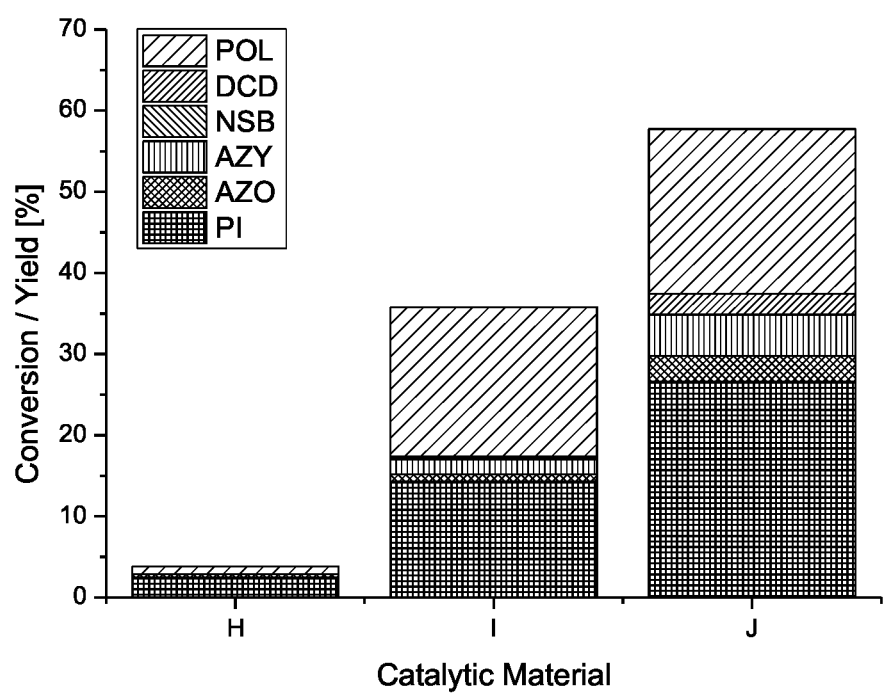
FIG. 1 shows the catalytic results for example catalysts H, I, J according to Table 2.

For X-Ray powder diffraction (XRPD) data were collected on a Bruker AXS D8 Advance. Cu Kα radiation was used in the data collection. The beam was narrowed using a collimator for line focus (Soller Slit, 2.5°) and a motorized divergence slit. Generator settings of 40 kV and 40 mA were used. Samples were gently ground in a mortar with a pestle and then packed in a round mount. The data collection from the round mount covered a 2θ range from 5° to 70° using a step scan with a step size of 0.02° and a count time of 0.2 s per step. DIFFRAC.EVA Software was used for all steps of the data analysis. The phases present in each sample were identified by search and match of the data available from International Centre for Diffraction Data (ICDD, Version 2015).

EXAMPLES

Batch Reactor Testing:

Screening in batch reactor was carried out in a series of single experiments, using batch autoclaves made from hastelloy C276. The general experimental procedure for each screening experiment was as follows:

In a first step a reaction mixture was prepared by dissolving nitrobenzene in chlorobenzene. The concentration of nitrobenzene in the reaction mixture was set to be between 1 wt % and 5 wt %. The respective amount of catalyst was placed into the empty reactor and heated to 160° C. and $10^{-1}$ bar for at least 12 h. In a second step the reaction mixture was charged into the reactor without lowering the temperature or opening the reactor using a specialized charging device. After charging the reaction mixture, the autoclave was heated or cooled to the desired temperature. In a final step the autoclave was pressurized with CO gas and nitrogen gas to the desired total pressure. The reaction mixture was stirred with 1000 rpm for the respective time.

The respective product spectrum was analyzed via a GC-MS unit (GC-MS from Agilent Technologies) equipped with FID, MS and TCD detectors. The total conversion of the reaction was calculated as the difference in starting and end concentration of the nitroaromatic compound divided by the starting concentration of the nitroaromatic compound. The concentration of the respective products in the reaction mixture was identified by GC analytic by using the respective response factors. The yield was determined by dividing the respective product concentration (in mmol/kg) by the starting concentration of the nitroaromatic compound (in mmol/kg) and multiplying the resulting value by the mol(s) of starting nitroaromatic compound needed to generate a mol of the respective product.

The difference between the combined yields of all products and the total calculated conversion is represented by the term "polymer". "Polymer" comprises the products formed which could not be analyzed by the applied GC-method.

Comparative Examples A to C

Synthesis of Oxides According to DE 1 810 828
Synthesis of $Pb_{0.3}Mn_{0.7}O_z$ For the preparation of the samples with a Mn:Pb ratio of 0.7:0.3, 0.1752 mol Mn as $Mn(NO_3)_2 \times 6H_2O$ and 0.075 mol Pb as $Pb(NO_3)_2$ were dissolved in 1 L of DI water under stirring. After the nitrates were dissolved, DI water was added up to 2.5 L. 1.04 mol activated carbon was added to the solution. The pH was adjusted to 10 by adding 8 wt % of a NaOH solution. The product precipitated, and the suspension was stirred for 30 minutes for aging.

The liquid was separated from the solids by decantation. DI water was added to the solids and stirred for 15 minutes. The procedure was repeated until the pH value was identical to the used DI water. The solids were separated by filtration and dried at 100° C. overnight.

Synthesis of $Fe_xMn_yO_z$

For the preparation of the MnFe samples with a Mn:Fe ratio of 0.8:0.2, the above described recipe was applied except the sources for Mn and Fe were not nitrates but chlorides (0.2 mol Mn as $MnCl_2 \times 4H_2O$ and 0.05 mol Fe as $FeCl_3 \times 6H_2O$).

1:1 physical mixtures of oxides with 5 wt % Rh or Pd impregnated on activated carbon were prepared according to GB1315813 A and catalytically tested. Table 2 shows the results of the reduction of nitrobenzene and insertion of CO into nitrosobenzene for the mixtures of (A) 5 wt % Pd on C and $Pb_{0.3}Mn_{0.7}O_x$, (B) 5 wt % Rh on C and $Pb_{0.3}Mn_{0.7}O_x$ and (C) 5 wt % Rh on C and $Fe_{0.2}Mn_{0.8}O_x$. Reaction conditions were p=100 barg, T=190° C. and 6 h reaction time. The physical mixture of (A) 5 wt. % Pd@C and $Pb_xMn_yO_z$ yielded no phenyl isocyanate at all, but the formation of nitrosobenzene, azo- and azoxybenzene was observed. However, the other two tested systems, (B) 5 wt % Rh@C and $Pb_xMn_yO_z$ and (C) 5 wt % Rh@C and $Fe_xMn_yO_z$, yielded the formation of Phenyl isocyanate, azo- and azoxybenzene as well as "polymer".

Comparative Examples D to G

The preparation of the comparative examples D to G was done by preparing single metal solutions as described in step (i) and impregnating the solutions on an activated carbon support as described in step (ii). The impregnation technique that was followed was incipient wetness impregnation. A drying Step (iia) at 80° C. was performed after the impregnation. The amount of metal deposited on the support was 5 wt % of the support mass. The respective metal containing components and solvents can be taken from Table 1.

TABLE 1

| Metal | Metal containing component | Solvent |
| --- | --- | --- |
| Rh | $Rh(NO_3)_3$ | $H_2O$ |
| Pb | $Pb(NO_3)_3$ | $H_2O$ |
| Sb | $Sb(CH_3COO)_3$ | Tataric acid (4M) |
| Sn | $SnC_2O_4$ | Nitric acid (35%) |
| Pd | $Pd(NO_3)_2$ | Nitric acid (35%) |
| In | $In(NO_3)_3$ | $H_2O$ |
| Ni | $Ni(NO_3)_2$ | $H_2O$ |
| Ga | $Ga(NO_3)_3$ | $H_2O$ |

Catalytic Results of Example A to G

Comparative examples A to G were catalytically tested. Table 2 shows the yields of the reduction of nitrobenzene (step 1) and the insertion of CO into nitrosobenzene to form phenyl isocyanate (step 2). For the mixtures of (A) 5 wt % Pd@C and $Pb_{0.3}Mn_{0.7}O_x$, (B) 5 wt % Rh@C and $Pb_{0.3}Mn_{0.7}O_x$ and (C) 5 wt % Rh@C and $Fe_{0.2}Mn_{0.8}O_x$ the reaction conditions were p=100 barg, T=190° C. and 6 h reaction time. The physical mixture of (A) 5 wt. % Pd@C and $Pb_xMn_yO_z$ yielded no phenyl isocyanate at all, but the formation of nitrosobenzene, azo- and azoxybenzene was observed. However, the other two tested systems, (B) 5 wt % Rh@C and $Pb_xMn_yO_z$ and (C) 5 wt % Rh@C and $Fe_xMn_yO_z$, yielded the formation of Phenyl isocyanate, azo- and azoxybenzene as well as "polymer".

For the single metal catalysts D to G, the reaction conditions were p=100 barg, T=160° C. and 4 h reaction time. No single metal catalysts yield any phenylisocyanate.

metal B was calculated according to the sum formula. After the drying step the composite materials of patent examples H to J received a combined reductive & thermal treatment for 5 h at 500° C. (steps iii & iv) using a muffle furnace and $N_2$ atmosphere. The respective support masses, concentrations and volumes can be taken from Table 3. The metal containing components and solvents can be taken from Table 1.

The preparation of the patent examples K to O was done by preparing single metal solutions as described in step (i) and impregnating the solutions consecutively on an oxidic support as described in step (ii). The impregnation technique that was followed was incipient wetness impregnation. For the examples K, L and M the single metal solution containing metal A was impregnated first. For the examples N and O the single metal solution containing metal B was impregnated first. In case of example N and O multiple impregnations for every solution were needed (see Table 3 for details).

TABLE 2

Results of the comparative examples.
PI = Phenyl isocyanate; AZO = Azobenzene; AZY = Azoxybenzene;
NSB = Nitrosobenzene; DCD = Diphenylcarbodiamide; POL = Polymer

| No. | Composition | PI [%] | AZO [%] | AZY [%] | NSB [%] | DCD [%] | POL [%] |
|---|---|---|---|---|---|---|---|
| A | Pd @ C + $Pb_{0.3}Mn_{0.7}O_x$ | 0 | 1.79 | 20.16 | 1.50 | 0 | 0 |
| B | Rh @ C + $Pb_{0.3}Mn_{0.7}O_x$ | 0.34 | 5.92 | 0.42 | 0 | 0 | 9.88 |
| C | Rh @ C + $Fe_{0.2}Mn_{0.8}O_x$ | 3.69 | 0.92 | 0.31 | 0 | 0 | 4.58 |
| D | 5 wt % Rh @ C | 0 | 0 | 0 | 0 | 0 | 0 |
| E | 5 wt % Pb @ C | 0 | 0 | 0.12 | 0 | 0 | 0.3 |
| F | 5 wt % Sb @ C | 0 | 0 | 0 | 0 | 0 | 0 |
| G | 5 wt % Sn @ C | 0 | 0 | 0 | 0 | 0 | 0 |

The results of comparative examples B and C indicate that both steps of the reaction occurred in a one pot synthesis by combining the functionalities of two catalysts, the oxide responsible for step 1 of the reaction and the base metal responsible for step 2 of the reaction.

H to O

The preparation of the patent examples H to J was done by preparing two separate single metal solutions as described step (i). After that a mixture was prepared from these solutions. The concentration of the single solutions and the respective volume used to prepare the mixture is shown in Table 3. The mixture was impregnated on an activated carbon support as described in step (ii). The impregnation technique that was followed was incipient wetness impregnation and a drying Step (iia) was performed at 80° C. after each impregnation step.

The amount of metal A deposited on the support was aimed to be 5 wt % of the supports mass. The amount of A drying Step (iia) was performed at 80° C. after each impregnation step. The amount of metal A deposited on the support was aimed to be 5 wt % of the support mass. The amount of metal B was calculated according to the sum formula. After the final drying step, the composite material was suspended in polyethylene glycol (polyol) and received a reductive treatment as described in step (iii). The reduction was done for 20 minutes at 200° C. using a 1000 W microwave oven and $N_2$ atmosphere. The reduced composite material was separated from the polyol and received a thermal treatment as described in step (iv) for 5 h at 500° C. using a muffle furnace and $N_2$ atmosphere.

The respective support masses, concentrations and volumes can be taken from Table 3. The metal containing components and solvents can be taken from Table 1.

TABLE 3

| No. | Composition $A_xB_y$ | 1 | 2 | 3 | 4 | 5 | 6 | 7 | 8 | 9 |
|---|---|---|---|---|---|---|---|---|---|---|
| H | $Rh_2Sn$ | C | 2.5 | 1.16 | 1.07 | 1 | 1 | 6.32 | 1 | a |
| I | RhSb | C | 2.5 | 1.16 | 1.11 | 1 | 1 | 1.29 | 1 | a |
| J | $RhPb_2$ | C | 2.5 | 1.16 | 1.32 | 1 | 1 | 3.04 | 1 | a |
| K | RhPb | $Al_2O_3$*) | 3 | 1.15 | 1.41 | 1 | 1 | 1.62 | 1 | b |
| L | $RhPb_2$ | $Al_2O_3$*) | 3 | 1.15 | 1.59 | 1 | 1 | 3.65 | 1 | b |

TABLE 3-continued

| Composition No. $A_xB_y$ | 1 | 2 | 3 | 4 | 5 | 6 | 7 | 8 | 9 |
|---|---|---|---|---|---|---|---|---|---|
| M RhPb$_2$ | Al$_2$O$_3$**) | 3 | 1.15 | 1.59 | 1 | 1 | 3.65 | 1 | b |
| N RhPb$_2$ | Mn$_2$O$_3$ | 33.5 | 1.148 | 17.75 | 3 | 1.5 | 27.17 | 5 | b |
| O RhSb | TiO$_2$***) | 2.5 | 1.16 | 1.11 | 2 | 1 | 1.30 | 2 | b |

1: Support material.
*)specific surface area: 100 m$^2$
**)specific surface area: 5 m$^2$
***)Rutile
2: Amount of support material [g].
3: Concentration of solution containing metal A [mol/L].
4: Total volume of solution containing metal A used for impregnation [ml].
5: Number of impregnation steps for solution containing metal A.
6: Concentration of solution containing metal B [mol/L].
7: Total volume of solution containing metal B used for impregnation [ml].
8: Number of impregnation steps for solution containing metal B.
9: Heating Method, a) Muffle Furnace 500° C.; 5 h; N$_2$ atmosphere. b) Microwave oven (1000 W) 200° C.; 20 minutes; N$_2$ atmosphere Catalytic Results of Examples H to O Table 4 and FIG. 1 show the results of the reduction of nitrobenzene and insertion of CO in nitrosobenzene. Reaction conditions were p=100 barg, T=160° C. and 4 h reaction time.

TABLE 4

Results of examples H to O

| No. | Composition | PI [%] | AZO [%] | AZY [%] | NSB [%] | DCD [%] | POL [%] |
|---|---|---|---|---|---|---|---|
| H | Rh$_2$Sn @ C | 2.45 | 0.40 | 0 | 0 | 0 | 0.95 |
| I | RhSb @ C | 14.27 | 0.89 | 1.87 | 0 | 0.30 | 18.43 |
| J | RhPb$_2$ @ C | 26.57 | 3.21 | 5.08 | 0 | 2.55 | 20.29 |
| K | RhPb @ Al$_2$O$_3$ | 3.60 | 1.98 | 0.34 | 0 | 0 | 4.68 |
| L | RhPb$_2$ @ Al$_2$O$_3$ | 4.50 | 2.60 | 1.69 | 0 | 0 | 6.09 |
| M | RhPb$_2$ @ Al$_2$O$_3$ | 2.46 | 0.14 | 0.35 | 0 | 0 | 2.24 |
| N | RhPb$_2$ @ Mn$_2$O$_3$ | 4.07 | 1.75 | 0.39 | 0 | 0 | 4.22 |
| O | RhSb @ TiO$_2$ | 2.26 | 0 | 0 | 0 | 0 | 1.18 |

The results show that—contrary to the single metal catalysts—the multi metallic catalysts yielded phenyl isocyanate as a product.

Figure 2:
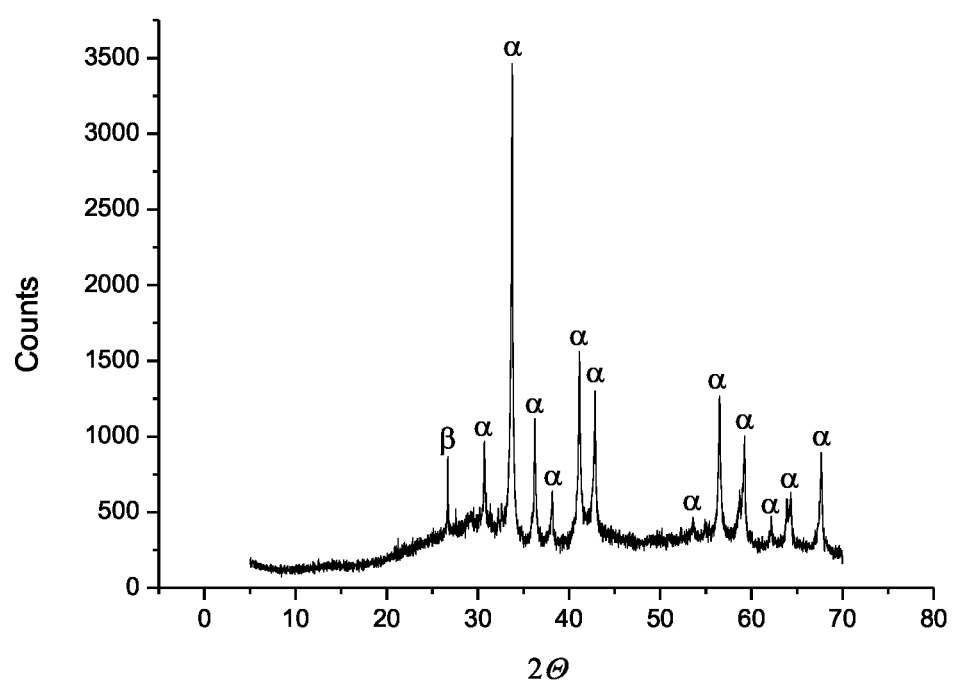
FIG. 2 shows the PXRD pattern of sample J α: Reflexes of $RhPb_2$. β: Reflex of graphite.
Figure 3:
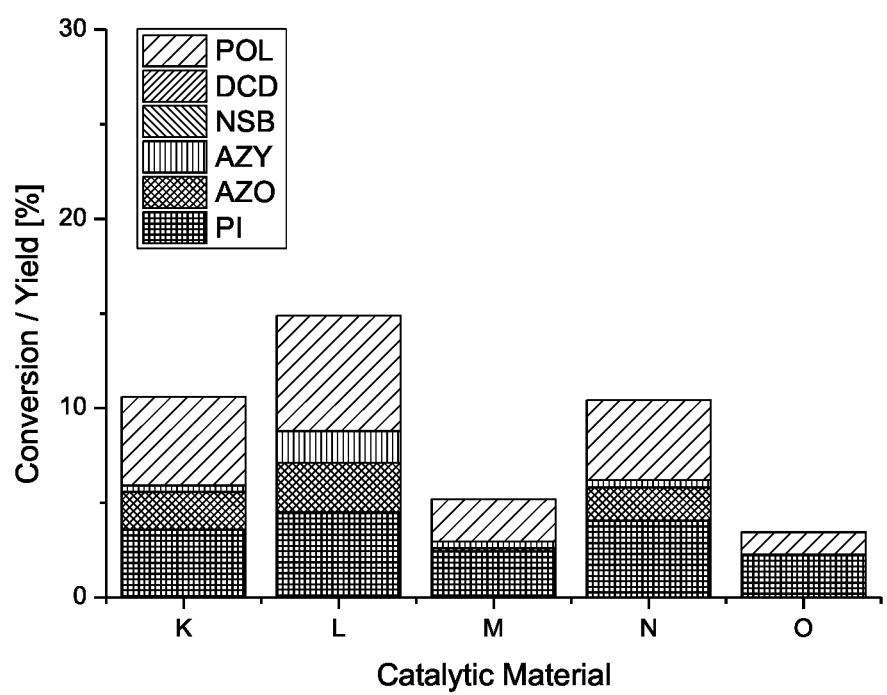
FIG. 3 shows the catalytic results for example catalysts K to O, according to Table 3.

FIG. 2 shows the PXRD pattern of sample J, proving that the multimetallic catalyst consists of the intermetallic compound RhPb$_2$ (α) on an amorphous carbon support. However, some traces of graphite (β) coming from the carbon support have been identified, too. In addition, the reflexes of graphite appeared as a consequence of the thermal treatment step.

Testing in a Continuous Reactor:

Screening in a continuous reactor was carried out in a series of experiments, using a trickle bed reactor system. The general experimental procedure for each screening experiment was as follows:

In a first step a reaction mixture was prepared by dissolving nitrobenzene or dinitrotoluene in chlorobenzene. The concentration of the respective nitroaromatic compound in the reaction mixture was set to be between 1 wt % and 3 wt %.

The reactor used were a tube reactor with a length of 40 cm an inner diameter of 0.4 cm. Inside the reactor 1 ml of the respective catalyst sieved to a fraction size of 125-160 μm was loaded. SiO$_2$ was used as pre- and post-bed inert material.

The reactor was heated to 160° C. in N$_2$ atmosphere for at least 12 h to remove residual water. After that the reactor temperature was set to the desired value.

In a following step the reaction mixture was mixed with CO or a mixture of CO & N$_2$ and fed to the reactor. The Liquid flow (LHSV) was set to be between 1 h$^{-1}$ and 4 h$^{-1}$. While the Gas flow (GHSV) was set to be between 500 & 3500 h$^{-1}$.

The obtained product mixture was collected over time and analyzed by GC.

All experimental details are summarized in Table 6.

The respective product spectrum was analyzed via a GC-MS unit (GC-MS from Agilent Technologies) equipped with FID, MS and TCD detectors. The total conversion of each reaction was calculated as difference of the reactor inlet (feed) concentration of the nitro aromatic compound and the concentration of the nitroaromatic compound in the product mixture divided by the starting concentration of the nitroaromatic compound. The concentration of the respective products in the product mixture was identified by GC analytic by using the respective response factors. The yield was determined by dividing the respective product concentration (in mmol/kg) by the concentration of the nitroaromatic compound (in mmol/kg) and multiplying the resulting value by the mol(s) of starting nitroaromatic compound needed to generate a mol of the respective product.

The difference between the combined yields of all products and the total calculated conversion of the nitroaromatic compounds is represented by the term "polymer". "Polymer" comprises the products formed which could not be analyzed by the applied GC-method.

The preparation of the patent examples H to BI was done by preparing separate single metal solutions as described step (i). After that a mixture was prepared from these solutions. The concentration of the single solutions and the respective volume used to prepare the mixture is shown in Table 5. The mixture was impregnated on various supports as described in step (ii). The impregnation technique that was followed was incipient wetness impregnation and a drying Step (iia) was performed at 80° C. after each impregnation step.

In some examples the support was prepared from mixture of two oxides. In this case the oxides have been mixed physically using a hand mill. The obtained oxidic mixture was calcined at 500° C. prior to the impregnation.

The amount of metal A deposited on the support was aimed to be between 1 and 5 wt % of the supports mass. The amount of metal B was calculated according to the sum formula. After the drying step the composite materials of patent examples H to BI received a reductive & thermal treatment for 5 h at 500° C. (steps iii & iv) using a muffle furnace and $N_2$ atmosphere. The respective support masses, concentrations and volumes can be taken from Table 5. The metal containing components and solvents can be taken from Table 1.

TABLE 5

| No. | Composition $A_xB_y$ | 1 | 2 | 3 | 4 | 5 | 6 | 7 | 8 | 9 |
|---|---|---|---|---|---|---|---|---|---|---|
| H | $Rh_2Sn$ | C | 2.5 | 0 | 1.16 | 1.07 | 1 | 1 | 6.32 | 1 |
| I | RhSb | C | 2.5 | 0 | 1.16 | 1.11 | 1 | 1 | 1.29 | 1 |
| J | $RhPb_2$ | C | 2.5 | 0 | 1.16 | 1.32 | 1 | 1 | 3.04 | 1 |
| O | RhSb | $TiO_2$**) | 2.5 | 0 | 1.16 | 1.11 | 2 | 1 | 1.30 | 2 |
| P | $Rh_2Sn$ | $TiO_2$**) | 2.5 | 0 | 1.16 | 1.07 | 2 | 1 | 6.32 | 2 |
| Q | RhGa | $TiO_2$**) | 8 | 0 | 1.15 | 3.38 | 2 | 2 | 1.94 | 2 |
| R | Rhin | $TiO_2$**) | 8 | 0 | 1.15 | 3.38 | 3 | 1 | 3.89 | 3 |
| S | $Pd_5Sb_2$ | $TiO_2$**) | 5 | 0 | 3.63 | 0.65 | 1 | 1 | 0.94 | 1 |
| T | $Pd_8Sb_3$ | $TiO_2$**) | 5 | 0 | 3.63 | 0.65 | 1 | 1 | 0.88 | 1 |
| U | $PdPb_2$ | $TiO_2$**) | 5 | 0 | 3.41 | 0.69 | 1 | 1.5 | 3.13 | 2 |
| V | RhSb | $TiO_2$**) | 21.2 | 0 | 1.16 | 1.78 | 1 | 1 | 2.05 | 1 |
| W | RhSb | $TiO_2$**) + 5% ZnO | 3.8 | 0.2 | 1 | 0.39 | 1 | 1 | 0.33 | 1 |
| X | RhSb | $TiO_2$**) + 10% ZnO | 10.5 | 1.17 | 1 | 1.14 | 1 | 1 | 1.14 | 1 |
| Y | RhSb | $TiO_2$**) + 20% ZnO | 3.2 | 0.8 | 1 | 0.39 | 1 | 1 | 0.33 | 1 |
| Z | RhSb | $TiO_2$**) + 30% ZnO | 2.8 | 1.2 | 1 | 0.39 | 1 | 1 | 0.33 | 1 |
| AA | RhSb | $TiO_2$**) + 40% ZnO | 2.4 | 1.6 | 1 | 0.39 | 1 | 1 | 0.33 | 1 |
| AB | RhSb | $TiO_2$**) + 50% ZnO | 1.75 | 1.75 | 1 | 0.34 | 1 | 1 | 0.29 | 1 |
| AD | RhSb | $TiO_2$**) + 67% ZnO | 0.85 | 1.65 | 1 | 0.24 | 1 | 1 | 0.21 | 1 |
| AE | RhSb | ZnO | 0 | 10 | 1 | 0.97 | 1 | 1 | 0.97 | 1 |
| AF | RhSb | $TiO_2$*) + 10% CaO | 3.51 | 0.39 | 1.13 | 0.33 | 1 | 1 | 0.38 | 1 |
| AG | RhSb | $TiO_2$**) + 10% CaO | 6.08 | 0.68 | 1.13 | 0.58 | 1 | 1 | 0.65 | 1 |
| AH | RhSb | $TiO_2$*) + 10% MgO | 3.89 | 0.43 | 1.13 | 0.37 | 1 | 1 | 0.42 | 1 |
| AI | RhSb | $TiO_2$**) + 10% MgO | 5.04 | 0.56 | 1.13 | 0.48 | 1 | 1 | 0.54 | 1 |
| AJ | RhSb | $TiO_2$*) + 10% $V_2O_5$ | 5.54 | 0.62 | 1.13 | 0.53 | 1 | 1 | 0.6 | 1 |
| AK | RhSb | $Mn_2O_3$ | 0 | 12.2 | 1.13 | 1.05 | 1 | 1 | 1.19 | 1 |
| AL | RhSb | $Mn_2O_3$ + 10% CaO | 5.49 | 0.61 | 1.13 | 0.52 | 1 | 1 | 0.59 | 1 |
| AM | RhSb | $Mn_2O_3$ + 45% $Fe_2O_3$ | 7.55 | 6.17 | 1.13 | 1.19 | 1 | 1 | 1.35 | 1 |
| AN | RhSb | $Mn_2O_3$ + 35% $Fe_2O_3$ | 8.99 | 4.84 | 1.13 | 1.19 | 1 | 1 | 1.34 | 1 |
| AO | RhSb | $Mn_2O_3$ + 25% $Fe_2O_3$ | 10.4 | 3.48 | 1.13 | 1.19 | 1 | 1 | 1.35 | 1 |
| AP | RhSb | $Mn_2O_3$ + 10% MgO | 5.03 | 0.56 | 1.13 | 0.48 | 1 | 1 | 0.54 | 1 |
| AQ | RhSb | $Mn_2O_3$ + 30% PbO | 12.3 | 5.28 | 1.13 | 1.51 | 1 | 1 | 1.71 | 1 |
| AR | RhSb | $Mn_2O_3$ + 10% ZnO | 6.44 | 0.72 | 1.13 | 0.61 | 1 | 1 | 0.69 | 1 |
| AS | RhSb | $MoO_3$ | 7.54 | 0 | 1.13 | 0.65 | 2 | 1 | 0.73 | 2 |
| AT | RhSb | $MoO_3$ + 10% CaO | 5.49 | 0.61 | 1.13 | 0.52 | 1 | 1 | 0.59 | 1 |
| AU | RhSb | $MoO_3$ + 10% MgO | 6.80 | 0.76 | 1.13 | 0.65 | 1 | 1 | 0.73 | 1 |
| AV | RhSb | $MoO_3$ + 10% ZnO | 7.25 | 0.81 | 1.13 | 0.69 | 1 | 1 | 0.78 | 1 |
| AW | RhSb | C | 3.52 | 0 | 1.16 | 0.29 | 1 | 1 | 0.34 | 1 |
| AX | RhSb | Elorit | 2 | 0 | 1.15 | 0.89 | 1 | 1 | 1.03 | 1 |
| AY | RhSb | $Bi_2O_3$ | 18.2 | 0 | 1.13 | 1.56 | 2 | 1 | 1.77 | 2 |
| AZ | RhSb | CaO | 10.0 | 0 | 1 | 0.97 | 1 | 1 | 0.97 | 1 |
| BA | RhSb | $Co_2O_3$ | 14.6 | 0 | 1.13 | 1.26 | 2 | 1 | 1.42 | 2 |
| BB | RhSb | $Cr_2O_3$ | 8.58 | 0 | 1.13 | 0.74 | 1 | 1 | 0.83 | 1 |
| BC | RhSb | $Fe_2O_3$ | 7.17 | 0 | 1.13 | 0.62 | 1 | 1 | 0.69 | 1 |
| BD | RhSb | $Fe_3O_4$ | 7.39 | 0 | 1.13 | 0.63 | 1 | 1 | 0.71 | 1 |
| BE | RhSb | $V_2O_5$ | 5.7 | 0 | 1.13 | 0.49 | 2 | 1 | 0.55 | 2 |
| BF | RhSb | $WO_3$ | 12.6 | 0 | 1.13 | 1.09 | 1 | 1 | 1.23 | 1 |
| BG | RhSb | $ZrO_2$ | 1 | 0 | 1.13 | 0.09 | 1 | 1 | 0.1 | 1 |
| BH | RhSb | $ZrO_2$ | 1 | 0 | 1.13 | 0.09 | 1 | 1 | 0.1 | 1 |
| BI | RhSb | $ZrWO_x$ | 5.79 | 0 | 1.13 | 0.5 | 1 | 1 | 0.56 | 1 |

1: Support material.
*)specific surface area: >5 $m^2$
**)Rutile
2: Amount of support material I [g].
3: Amount of support material II [g].
4: Concentration of solution containing metal A [mol/L].
5: Total volume of solution containing metal A used for impregnation [ml].
6: Number of impregnation steps for solution containing metal A.
7: Concentration of solution containing metal B [mol/L].
8: Total volume of solution containing metal B used for impregnation [ml].
9: Number of impregnation steps for solution containing metal B.

TABLE 6

Overview about experimental parameters.

| # | 1a | 2a | 3a | 4a | 5a | 6a | 7a | 8a |
|---|---|---|---|---|---|---|---|---|
| a | NB | 1 | 160 | 100 | 100 | 0 | 4 | 2000 |
| b | NB | 1 | 120 | 100 | 100 | 0 | 4 | 2000 |
| c | NB | 1 | 80 | 100 | 100 | 0 | 4 | 2000 |
| d | 2,4-DNT | 1 | 60 | 100 | 100 | 0 | 4 | 2000 |
| e | 2,4-DNT | 1 | 80 | 100 | 100 | 0 | 4 | 2000 |
| f | 2,4-DNT | 1 | 100 | 100 | 100 | 0 | 4 | 2000 |
| g | 2,4-DNT | 1 | 120 | 100 | 100 | 0 | 4 | 2000 |
| h | 2,4-DNT | 1 | 80 | 100 | 100 | 0 | 1 | 2000 |
| i | 2,4-DNT | 1 | 80 | 100 | 100 | 0 | 4 | 500 |
| j | 2,4-DNT | 1 | 80 | 100 | 100 | 0 | 1 | 500 |
| k | 2,4-DNT | 1 | 120 | 100 | 100 | 0 | 1 | 2000 |
| l | 2,4-DNT | 1 | 120 | 100 | 100 | 0 | 4 | 500 |
| m | 2,4-DNT | 1 | 120 | 100 | 100 | 0 | 1 | 500 |
| n | 2,4-DNT | 1 | 130 | 100 | 100 | 0 | 4 | 2000 |
| o | 2,4-DNT | 1 | 140 | 100 | 100 | 0 | 4 | 2000 |
| P | 2,4-DNT | 1 | 120 | 100 | 100 | 0 | 1 | 2750 |
| q | 2,4-DNT | 1 | 120 | 100 | 100 | 0 | 1 | 3500 |
| r | 2,4-DNT | 1 | 140 | 100 | 100 | 0 | 3 | 2000 |
| s | 2,4-DNT | 1 | 140 | 100 | 100 | 0 | 2 | 2000 |
| t | 2,4-DNT | 1 | 140 | 100 | 100 | 0 | 1 | 2000 |
| v | 2,4 DNT & 2,6 DNT | 3 | 140 | 50 | 100 | 0 | 1 | 2000 |

1a: Feed stock
NB) Nitrobenzene
2,4-DNT)2,4-Dinitrotoluene
2,4-DNT & 2,6-DNT) Mixture of 20 wt % 2,6-DNT & 80 wt % 2,4-DNT
2a: Feed concentration [wt %]
3a: Temperature [° C.]
4a: Total Pressure [bar]
5a: Concentration of CO [vol %]
6a: Concentration of N2 [vol %]
7a: LHSV (Liquid hourly space velocity) [$h^{-1}$]
8a: GHSV (Gas hourly space velocity) [$h^{-1}$]

TABLE 7

Results of catalytic tests in trickle bed set up with nitro benzene:
PI = Phenyl isocyanate; AZO = Azobenzene;
AZY = Azoxybenzene; NSB = Nitrosobenzene;
DCD = Diphenylcarbodiamide;
POL = Polymer. X = Total conversion.

| No. | # | PI [%] | AZO [%] | AZY [%] | NSB [%] | DCD [%] | POL [%] |
|---|---|---|---|---|---|---|---|
| I | a | 32.01 | 1.71 | 0.00 | 0 | 1.09 | 65.20 |
| J | a | 1.67 | 1.69 | 18.78 | 0 | 0.03 | 58.53 |
| O | a | 49.07 | 2.31 | 0.00 | 0 | 4.10 | 44.53 |
| H | b | 7.54 | 0.30 | 0.48 | 0 | 0.01 | 10.43 |
| O | b | 72.20 | 2.32 | 1.73 | 0 | 1.02 | 18.96 |
| H | c | 0.79 | 0.03 | 0.09 | 0 | 0 | 2.77 |
| O | c | 9.93 | 0.73 | 0.51 | 0 | 0 | 5.31 |

The results show, that isocynates can be produced from nitro aromatic compounds in a continuous process.

TABLE 8

Results of catalytic tests in trickle bed set up with DNT Feed stock:
TDI = 2,4-Toluenediisocyanate; TNI = Toluenenitroisocyanates,
AZOC = Azo compounds; AZYC = Azoxy compounds;
NSC = Nitroso compounds; AC = Amine compounds; POL = Polymer.

| No | # | TDI [%] | TNI [%] | AZOC [%] | AZYC [%] | NSC [%] | AC [%] | POL [%] |
|---|---|---|---|---|---|---|---|---|
| O | d | 0.05 | 11.43 | 2.01 | 2.75 | 0.06 | 1.01 | 1.43 |
| O | e | 0.15 | 16.65 | 1.57 | 2.74 | 0.15 | 0.97 | 1.25 |
| O | f | 0.89 | 33.85 | 1.54 | 3.60 | 0.39 | 1.08 | 3.10 |
| O | g | 3.31 | 55.68 | 0.99 | 2.59 | 0.69 | 1.05 | 1.15 |
| O | h | 0.48 | 25.22 | 1.03 | 1.55 | 0.19 | 1.01 | 1.62 |
| O | i | 0.00 | 4.88 | 0.83 | 0.32 | 0.20 | 0.81 | 2.79 |
| O | j | 0.04 | 6.17 | 0.81 | 0.43 | 0.18 | 0.84 | 6.82 |
| O | k | 35.57 | 48.82 | 0.27 | 0.98 | 0.41 | 0.16 | 10.67 |
| O | l | 2.73 | 48.11 | 0.80 | 2.03 | 0.76 | 1.02 | 1.23 |
| O | m | 4.28 | 48.85 | 0.76 | 1.95 | 0.68 | 0.93 | 1.23 |
| O | n | 5.02 | 56.79 | 0.70 | 2.12 | 0.78 | 0.89 | 8.99 |
| O | o | 12.90 | 71.06 | 0.48 | 2.09 | 0.98 | 0.74 | 1.20 |
| O | p | 14.16 | 70.82 | 0.40 | 1.58 | 0.54 | 0.68 | 3.60 |
| O | q | 14.55 | 72.89 | 0.42 | 1.66 | 0.55 | 0.76 | 1.45 |
| O | r | 0.00 | 2.29 | 0.65 | 0.36 | 0.32 | 0.74 | 3.51 |
| O | s | 19.26 | 69.01 | 0.28 | 1.35 | 0.72 | 0.69 | 3.99 |
| O | t | 47.52 | 36.47 | 0.19 | 0.71 | 0.36 | 0.20 | 14.68 |
| P | d | 0.04 | 5.87 | 0.95 | 1.28 | 0.00 | 1.73 | 1.26 |
| P | e | 0.04 | 5.03 | 1.40 | 1.14 | 0.31 | 1.44 | 2.17 |
| P | f | 0.11 | 8.75 | 1.81 | 1.53 | 0.89 | 1.53 | 5.71 |
| P | g | 0.12 | 7.44 | 1.50 | 0.66 | 1.34 | 1.48 | 5.15 |
| P | h | 0.00 | 1.09 | 1.40 | 0.31 | 0.48 | 1.43 | 4.02 |
| P | i | 0.00 | 0.14 | 0.77 | 0.00 | 0.14 | 0.80 | 1.59 |
| P | j | 0.00 | 0.31 | 0.94 | 0.09 | 0.21 | 1.01 | 5.70 |
| P | k | 0.40 | 9.74 | 1.48 | 1.55 | 1.75 | 2.54 | 17.54 |
| P | l | 0.00 | 2.35 | 1.06 | 0.21 | 1.00 | 1.12 | 4.34 |
| P | m | 0.08 | 4.41 | 1.21 | 0.44 | 1.27 | 1.34 | 5.76 |
| P | n | 0.08 | 4.54 | 1.21 | 0.49 | 1.53 | 1.31 | 18.32 |
| P | o | 0.15 | 7.65 | 1.54 | 0.75 | 2.13 | 1.60 | 7.80 |
| P | p | 0.15 | 4.70 | 2.81 | 0.77 | 1.24 | 3.69 | 11.38 |
| P | q | 0.14 | 4.29 | 3.02 | 0.83 | 1.08 | 4.01 | 12.78 |
| P | r | 0.00 | 0.04 | 0.60 | 0.00 | 0.00 | 0.76 | 2.17 |
| P | s | 0.16 | 5.42 | 1.87 | 0.66 | 1.69 | 2.32 | 8.43 |
| P | t | 0.27 | 7.66 | 2.41 | 1.14 | 1.29 | 3.24 | 18.15 |

The results show, that nitroaromatic compounds containing multiple nitrogroups can be converted into isocyanates directly. Since the number of structural isomers is increasing with the number of nitro groups the yields are presented as group yields.

As stated above, the intermediates like nitroso compounds or partially carbonylated nitro aromatic compounds like Toluenenitroisocyanates (TNI) may be obtained as a result of an incomplete reaction, but is still considered as a successful outcome in terms of this invention.

TABLE 9

Results of catalytic tests in trickle bed set up with DNT Feed stock:
TDI = 2,4 + 2.6-Toluenediisocyanate; TNI = (isomers of Toluenenitroisocyanate, Byproducts = Azo compounds, Azoxy compounds, Nitroso compounds, Amine compounds, Polymer.

| No | # | TDI | TNI | Byproducts |
|---|---|---|---|---|
| Q | v | 0.00 | 0.08 | 7.02 |
| R | v | 0.06 | 2.04 | 17.47 |
| S | v | 0.00 | 1.57 | 11.66 |
| T | v | 0.00 | 2.24 | 5.15 |
| U | v | 0.00 | 0.12 | 5.17 |
| V | v | 7.00 | 41.03 | 20.4 |
| W | v | 8.48 | 42.88 | 44.37 |
| X | v | 33.81 | 59.80 | 5.81 |
| Y | v | 16.91 | 39.11 | 40.35 |
| Z | v | 19.11 | 42.01 | 35.71 |
| AA | v | 23.51 | 40.92 | 32.51 |
| AB | v | 11.34 | 58.96 | 23.51 |
| AD | v | 19.80 | 47.35 | 29.94 |
| AE | v | 1.68 | 29.90 | 43.88 |
| AF | v | 12.38 | 61.52 | 16.15 |
| AG | v | 18.12 | 71.15 | 5.18 |
| AH | v | 10.09 | 60.85 | 13.53 |
| AI | v | 23.67 | 64.83 | 10.08 |
| AJ | v | 5.73 | 44.05 | 28.61 |

TABLE 9-continued

Results of catalytic tests in trickle bed set up with DNT Feed stock: TDI = 2,4 + 2,6-Toluenediisocyanate; TNI = (isomers of Toluenenitroisocyanate, Byproducts = Azo compounds, Azoxy compounds, Nitroso compounds, Amine compounds, Polymer.

| No | # | TDI | TNI | Byproducts |
|---|---|---|---|---|
| AK | t | 4.11 | 45.56 | 23.93 |
| AL | v | 18.21 | 73.10 | 3.70 |
| AM | v | 2.34 | 46.49 | 9.53 |
| AN | v | 2.05 | 43.53 | 8.41 |
| AO | v | 2.05 | 44.31 | 8.37 |
| AP | v | 1.77 | 37.36 | 17.05 |
| AQ | v | 0.00 | 0.21 | 15.97 |
| AR | v | 13.60 | 57.68 | 17.72 |
| AS | v | 0.02 | 2.03 | 3.84 |
| AT | v | 0.00 | 3.36 | 9.63 |
| AU | v | 1.65 | 38.77 | 8.90 |
| AV | v | 0.33 | 16.63 | 11.89 |
| AW | v | 5.56 | 32.18 | 51.16 |
| AX | v | 0.19 | 12.07 | 12.19 |
| AY | v | 0.00 | 0.17 | 13.84 |
| AZ | v | 0.00 | 15.81 | 25.41 |
| BA | v | 1.98 | 34.08 | 17.09 |
| BB | v | 0.00 | 0.24 | 12.38 |
| BC | v | 1.72 | 35.88 | 15.64 |
| BD | v | 1.27 | 31.77 | 13.40 |
| BE | v | 0.00 | 1.91 | 6.57 |
| BF | v | 3.30 | 46.46 | 14.42 |
| BG | v | 0.50 | 16.21 | 30.92 |
| BH | v | 0.01 | 3.07 | 22.84 |
| BI | v | 0.00 | 0.00 | 8.61 |

The invention claimed is:

1. A catalyst for direct carbonylation of a nitroaromatic compound to a corresponding aromatic isocyanate, the catalyst containing a multi metallic material comprising one or more binary intermetallic phases of formula $A_xB_y$ wherein:
   A is Rh,
   B is at least one element selected from the group consisting of Sn, Sb, Pb,
   x is in the range 0.1-10,
   y is in the range 0.1-10.

2. The catalyst according to claim 1, wherein the multi metallic material comprises at least one component C, wherein component C contains A or B not being part of the intermetallic compound $A_xB_y$.

3. The catalyst according to claim 1, wherein the multi metallic material comprises at least one component C, wherein component C contains at least one elements selected from the group consisting of O, N, C, H, Li, Na, K, Rb, Cs, Mg, Ca, Sr and Ba.

4. The catalyst according to claim 1, wherein the multi metallic material comprises at least one binary intermetallic crystalline phases selected from the group consisting of RhPb, RhPb2, Rh4Pb5, Rh2Sn, RhSn, RhSn2, RhSn4, Rh2Sb, RhSb, RhSb2, RhSb3.

5. The catalyst according to claim 4, wherein the multi-metallic material comprises at least one binary intermetallic crystalline phases selected from the group consisting of RhPb, RhPb2, RhSb, Rh2Sb, RhSb2 and Rh2Sn.

6. The catalyst according to claim 1 wherein the multi metallic material is deposited on a carrier material.

7. A process for the production of a catalyst as defined in claim 6 comprising steps (i) to (iv):
   (i) providing one or more precursors for elements A and B and optionally component C in the form of a solution;
   (ii) depositing the metal precursors on a support material to form a composite material;
   (iii) reductive treatment of the composite material;
   (iv) thermal treatment of the composite material.

8. The process according to claim 7, wherein the solution comprises one or more solvents selected from the group consisting of water, alcohols, polyols, acids and bases.

9. The process according to claim 7 comprising the steps:
   (iii) contacting the support material containing the metal precursors with one or more of reducing agents in solid, liquid or gaseous form selected from alcohols, hydrocarbons, amines, polyols, Zn-powder, $H_2$, CO, $CH_4$ and $C_2H_4$, and
   (iv) reducing the support material containing the metal precursors by thermal reduction under chemically inert conditions.

10. The process according to claim 9, wherein step (iii) and (iv) are carried out in one single step.

* * * * *